United States Patent
Espinos Ferri et al.

(10) Patent No.: US 10,717,701 B2
(45) Date of Patent: Jul. 21, 2020

(54) PREPARATION OF CYCLIC ALLYLIC NITRO COMPOUNDS

(71) Applicant: International Flavors & Fragrances Inc., New York, NY (US)

(72) Inventors: Estela Espinos Ferri, Moncofar (ES); Ana Maria Collado Perez, Benicarlo (ES); Ian R. Baxendale, Durham (GB); James S. Sharley, Biggleswade (GB)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 16/604,227

(22) PCT Filed: Apr. 5, 2018

(86) PCT No.: PCT/US2018/026212
§ 371 (c)(1),
(2) Date: Oct. 10, 2019

(87) PCT Pub. No.: WO2018/187542
PCT Pub. Date: Oct. 11, 2018

(65) Prior Publication Data
US 2020/0157038 A1 May 21, 2020

Related U.S. Application Data

(60) Provisional application No. 62/483,014, filed on Apr. 7, 2017.

(51) Int. Cl.
*C07C 205/03* (2006.01)

(52) U.S. Cl.
CPC .................. *C07C 205/03* (2013.01)

(58) Field of Classification Search
CPC ...................................... C07C 205/03
See application file for complete search history.

(56) References Cited

U.S. PATENT DOCUMENTS 9,085,516 B2 * 7/2015 Muratore ............... A61Q 13/00

OTHER PUBLICATIONS

Tamura et al. Facile Synthesis of Allylic Nitro Compounds by N,N-Dimethylethylenediamine-Catalyzed Condensation of Aliphatic and Alicyclic Ketones with Primary Nitroalkanes. Journal of Organic Chemistry, vol. 51, 4368-4375. (Year: 1986).*
Gu et al. A General, Scalable, Organocatalytic Nitro-Michael Addition to Enones: Enantioselective Access to All-Carbon Quaternary Stereocenters. Organic Letters, vol. 17, 1505-1508. (Year: 2015).*

* cited by examiner

*Primary Examiner* — Sikarl A Witherspoon
(74) *Attorney, Agent, or Firm* — Martin Zhang; Xufan Tseng; Elizabeth M. Stover

(57) ABSTRACT

Amine-catalyzed formation of cyclic allylic nitro compounds via nitro-aldol reaction is disclosed. A greener solvent and a cheaper, more robust catalyst than in previous reports are used in the nitro-aldol reaction. After screening a range of catalysts the reaction is developed as a selective method of synthesis of α-dehydroherbac and the scope is demonstrated with a small collection of additional substrates.

14 Claims, 1 Drawing Sheet

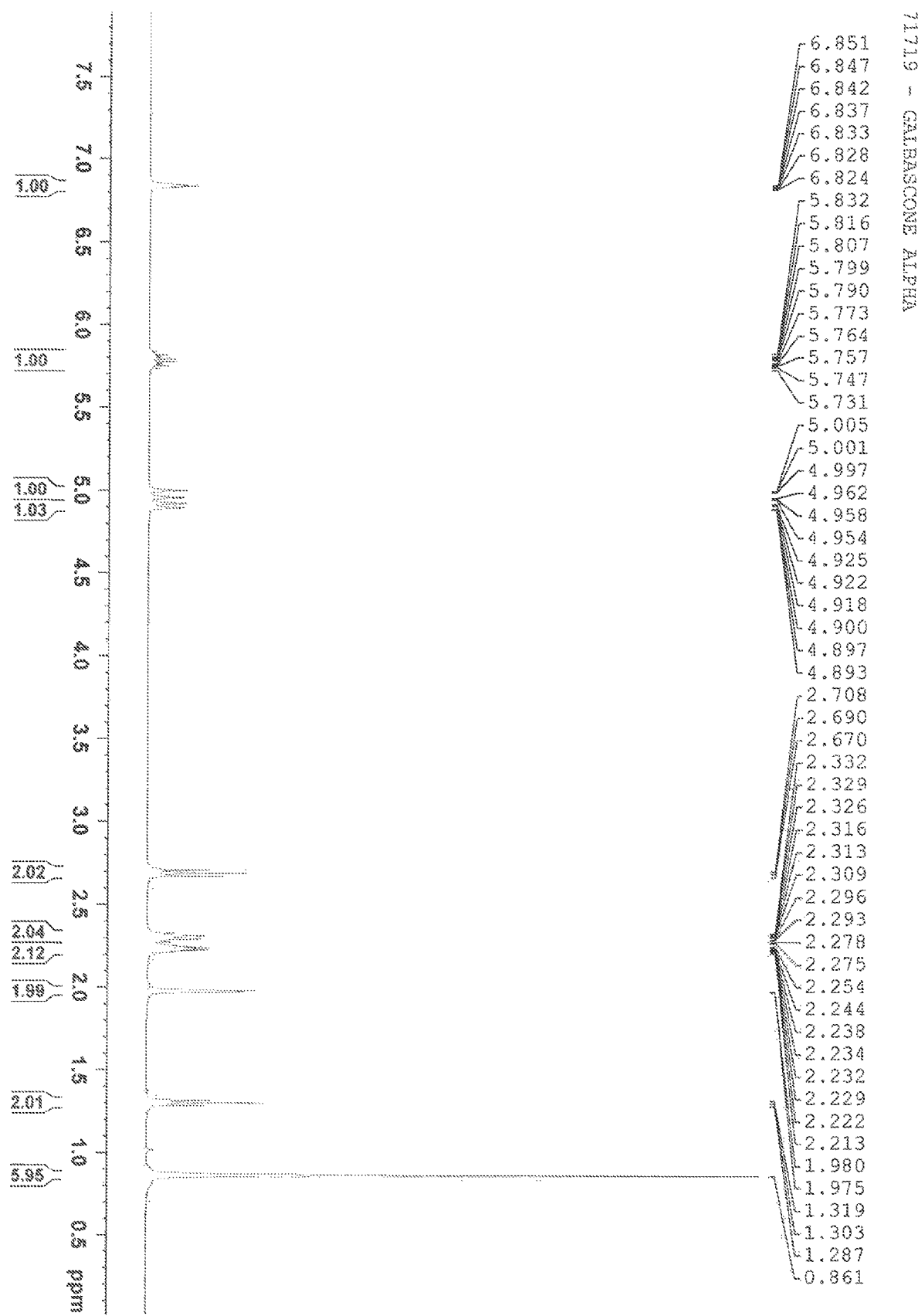

PREPARATION OF CYCLIC ALLYLIC NITRO COMPOUNDS

CROSS REFERENCE TO RELATED APPLICATIONS

This application is a national stage entry under 35 USC 371 for International Application No. PCT/US2018/026212, filed Apr. 5, 2018, which claims priority to U.S. Application No. 62/483,014, filed on Apr. 7, 2017. The contents of both applications are incorporated herein by reference in their entirety.

FIELD OF THE INVENTION

The present invention relates to synthesis of cyclic allylic nitro compounds, in particular synthesis of cyclic allylic nitro compounds using nitro-aldol reaction.

BACKGROUND OF THE INVENTION

Allylic nitro compounds 1 are a synthetically versatile class of structures capable of delivering a wide range of products possessing important structural motifs (Scheme 1). These include α,β-unsaturated ketones 2, allylic amines 3, allylic nitriles 4, unsaturated β-nitro alcohols 5, unsaturated β-amino alcohols 6, unsaturated α-nitro ketones 7, 2-nitro-1,3-dienes 8 as well as further functionalized products 9.

enediamine 12 could be used as a catalyst for the formation of allylic nitro compounds from ketones and primary nitroalkanes (Scheme 2).

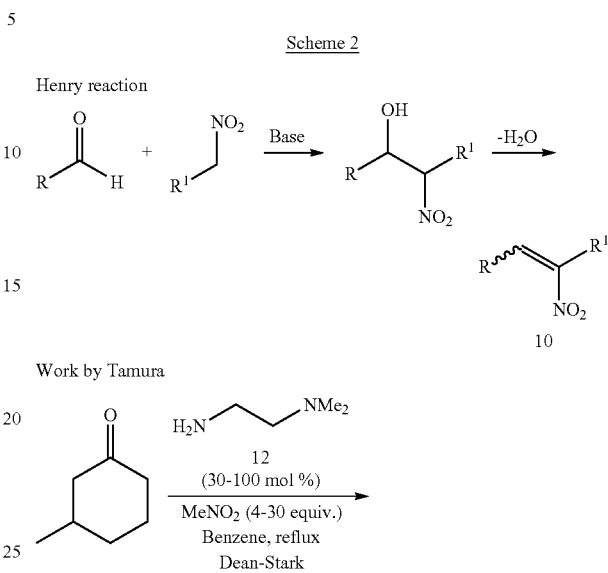

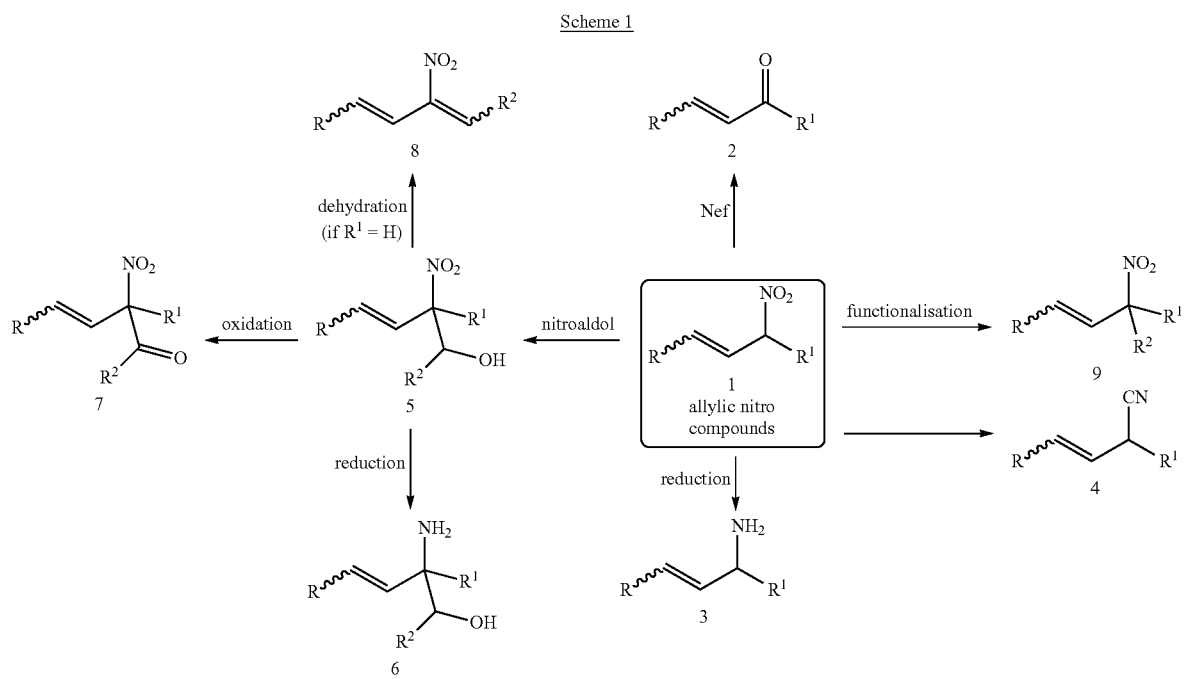

The nitro-aldol or Henry reaction is a widely used tool for the construction of conjugated nitroalkanes 10 (Henry, *Compt. Rend.* 1895, 120, 1265; Wang, Henry Reaction. In *Comprehensive Organic Name Reactions and Reagents*, John Wiley & Sons, Inc.: 2010). In 1982, Barton et al. detailed the use of imine catalysis for irregular nitro-aldol reactions which gave allylic nitro compounds 11 useful in the synthesis of corticosteroids (Barton et al., *J. Chem. Soc., Chem. Commun.* 1982, 551-552). This was later explored in more detail by Tamura et al. (*J. Org. Chem.* 1986, 51, 4368-4375). Where it was shown that N,N-dimethylethyl- -continued

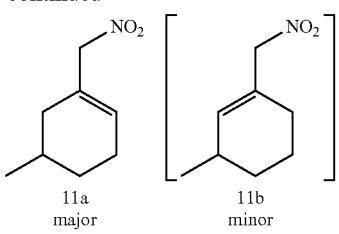

The methodology developed by Barton and Tamura was used recently for the synthesis of symmetrical cycloalkene allylic nitro compounds (Umemiya et al., *Chem. Eur. J.* 2014, 20, 15753-59). For all of these developed nitro-aldol reactions, benzene was used as a solvent for azeotropic removal of water formed during the reaction. However, the use of benzene is now heavily regulated. In addition, it has received no attention with regards to the selective preparation of asymmetric cyclic allylic nitro compounds since these initial discoveries in 1982/1986. There is a need to develop a green and efficient process to prepare cyclic allylic nitro compounds.

SUMMARY OF THE INVENTION

The present application discloses a method of preparing cyclic allylic nitro compounds from corresponding cyclic ketones and nitroalkanes, in particular, selective synthesis of 5,5-dimethyl-1-(1-nitroethyl)cyclohex-1-ene, and in turn, coupling this methodology with a subsequent Nef reaction to deliver dehydroherbac with high selectivity towards desired α-dehydroherbac 13a, an important intermediate in the flavor and fragrance industry useful for preparing α-Galbascone 14a (Scheme 3).

In one aspect, the present invention provides a method of preparing a cyclic allylic nitro compound, comprising a nitro-aldol reaction between a cyclic ketone and nitroalkane in the presence of a nitro-aldol catalyst in a solvent.

Scheme 3: Dehydroherbac 13a,
used in the industrial synthesis of α-Galbascone

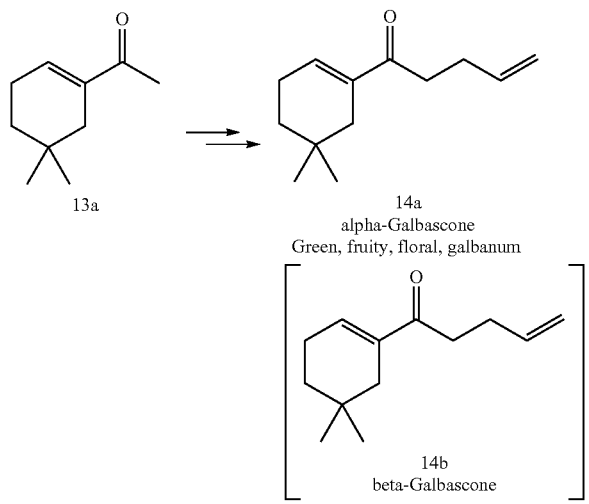

The cyclic allylic nitro compound is a compound of Formula (I),

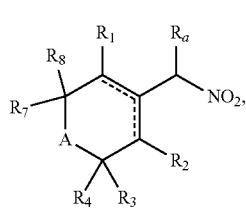

in which one of the two ═══ is a double bond, and the other is a single bond, $R_a$ is H or methyl, at least one of $R_1$ and $R_2$ is hydrogen, the other one is hydrogen or methyl, A is $(CR_5R_6)_n$, n is an integer from 0 to 20, and each of $R_3$, $R_4$, $R_5$, $R_6$, $R_7$, and $R_8$, independently, is hydrogen, $C_1$-$C_4$ alkyl, or $C_2$-$C_4$ alkenyl.

The cyclic ketone is a compound of Formula (II),

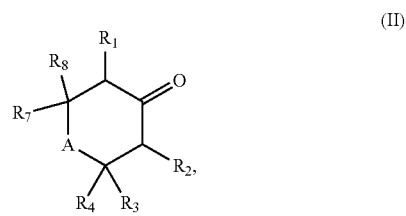

in which $R_1$-$R_4$, A, $R_7$, and $R_8$ are define above.

The nitro-aldol catalyst can be an amine catalyst of Formula (III):

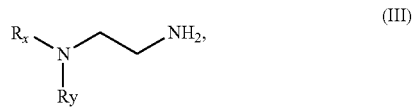

in which each of Rx and Ry, independently, is $C_1$-$C_4$ alkyl, or Rx and Ry, together with nitrogen atom to which they attached, form a pyrrolidine ring or a piperidine ring.

The nitroalkane is typically nitroethane or nitromethane. The solvent is a $C_2$-$C_3$ alkyl acetate (e.g., ethyl acetate and isopropyl acetate).

In another aspect, the present invention provides a method of preparing α-dehydroherbac (i.e., 1-(5,5-Dimethylcyclohex-1-en-1-yl)ethanone), comprising (a) obtaining 5,5-dimethyl-1-(1-nitroethyl)cyclo-hex-1-ene according to the above-mentioned nitro-aldol reaction, and (b) a Nef reaction of 5,5-dimethyl-1-(1-nitroethyl)cyclohex-1-ene to obtain α-dehydroherbac.

In still another aspect, the present invention provides a method of preparing α-Galbascone, comprising (c) obtaining α-dehydroherbac via the above-mentioned nitro-aldol reaction and Nef reaction, and (d) converting α-dehydroherbac to α-Galbascone.

Other aspects and advantages of the present invention can be better appreciated in view of the detailed description and claims.

DETAILED DESCRIPTION OF THE INVENTION

The present invention is based on a surprising discovery of a green and sustainable process for efficiently preparing a cyclic allylic nitro compound via a nitro-aldol reaction.

In one aspect, the present invention provides a method of preparing a cyclic allylic nitro compound, comprising a nitro-aldol reaction between a cyclic ketone and a nitroalkane in the presence of a nitro-aldol catalyst in a solvent.

Suitable nitro-aldol catalysts include ionic bases such as alkali metal oxides or hydroxides (e.g., MgO, CaO, SrO, BaO, $La_2O_3$, $ZrO_2$, ZnO, LiOH, NaOH, KOH, $Ca(OH)_2$, $Mg(OH)_2$, $Ba(OH)_2$, $Sr(OH)_2$, γ-Alumina, MgO-alumina, and KOH/alumina), alkoxides, carbonates ($MgCO_3$, $BaCO_3$, $CaCO_3$, and $SrCO_3$), sources of fluoride anion (e.g. KF/alumina, tetra-n-butylammonium fluoride), polymer supported amines, and amine catalysts such as 1,1,3,3-Tetramethylguanidine (TMG), N, N-Diisopropylethylamine (DIPEA), 1,8-Diazabicyclo[5.4.0]undec-7-ene (DBU), 1,5-Diazabicyclo[4.3.0]non-5-ene (DBN), and quinine and derivatives. See Akutu et al., Applied Catalysis A: General 2003, 247(1), 65-74; and Palacios et al., Archive for Organic Chemistry 2005 (9), 405-14.

In some embodiments, the nitro-aldol catalyst is an amine catalyst. Examples include:

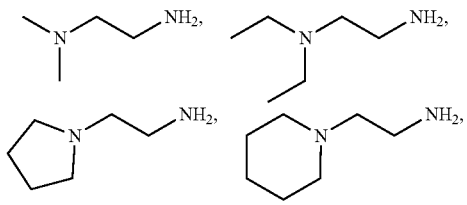

and combinations thereof.

In some embodiments, the amount of the nitroalkane is at least 1 equivalent (e.g., 1 to 20 equivalents with a lower limit of 1.5, 2, 2.5, 3, or 5 equivalents and an upper limit of 15, 12, 10, or 8 equivalents) relative to the cyclic ketone. In other embodiments, the amount of the nitro-aldol (e.g., an amine catalyst) is up to 1 equivalent (e.g., 0.01 to 1 equivalents with a lower limit of 0.02, 0.05, 0.1, or 0.2 equivalents and an upper limit of 1, 0.8, 0.6, or 0.5 equivalents), also relative to the cyclic ketone.

In some embodiments, the nitro-aldol reaction is conducted under reflux and water is removed, e.g., via azeotropic distillation or molecular sieve water absorption. In a preferred embodiment, a Dean-Stark device is used in the azeotropic distillation.

In some embodiments, the nitro-aldol reaction product is isolated by distillation, e.g., under a reduced pressure (0.1 to 100 millibars with a lower limit of 0.2, 0.5, or 1 millibars and an upper limit of 80, 50, 30, or 20 millibars).

In a preferred embodiment, an acid wash is conducted prior to isolation of the nitro-aldol product by distillation.

In some embodiments, the nitro-aldol catalyst (e.g., an amine catalyst) is added portion-wise, and the reaction time is 36 hours or less (e.g., 1-36 hours with a lower limit of 1, 2, 4, 6, 8, or 10 hours and an upper limit of 36, 30, 28, or 24 hours).

In some embodiments, the cyclic ketone is any one selected from the group consisting of:

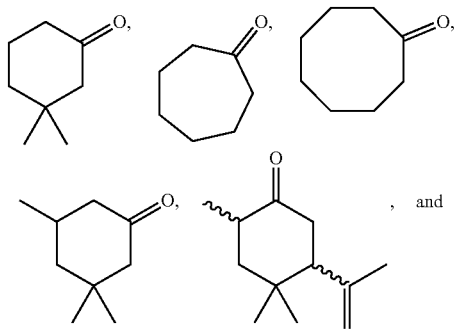

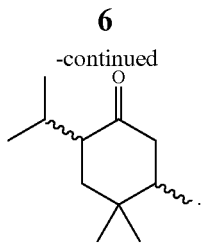

In a preferred embodiment, the cyclic allylic nitro compound is 5,5-dimethyl-1-(1-nitroethyl)cyclohex-1-ene, the cyclic ketone is 3,3-dimethylcyclohexanone, and the nitroalkane is nitroethane.

In another aspect, the present invention provides a method of preparing α-dehydroherbac, comprising (a) obtaining 5,5-dimethyl-1-(1-nitroethyl)cyclohex-1-ene according to the above-mentioned nitro-aldol reaction, and (b) a Nef reaction of 5,5-dimethyl-1-(1-nitroethyl)cyclohex-1-ene to obtain α-dehydroherbac.

In some embodiments, the Nef reaction comprises nitronate salt formation with NaOH, followed by treatment with sulfuric acid, hydrochloric acid, or both.

In still another aspect, the present invention provides a method of preparing α-Galbascone, comprising (c) obtaining α-dehydroherbac via the above-mentioned nitro-aldol reaction and Nef reaction, and (d) converting α-dehydroherbac to α-Galbascone.

In some embodiments, the present invention further provides combinations of any of the preferred embodiments disclosed here.

The term "alkyl", as used herein, means a straight or branched-chain saturated aliphatic hydrocarbon group containing from 1 to 10 carbon atoms, preferably 1 to 8 carbon atoms, sometimes more preferably 1 to 6 carbon atoms ("lower alkyl"), and sometimes more preferably 1 to 4 carbon atoms ("$C_1$-$C_4$ alkyl"), which is connected with the rest of the molecular moiety through a single bond. Representative examples of alkyl include, but are not limited to, methyl, ethyl, n-propyl, iso-propyl, n-butyl, sec-butyl, iso-butyl, tert-butyl, etc.

The term "alkenyl", as used herein, means a straight or branched-chain unsaturated aliphatic hydrocarbon group containing from 2 to 10 carbon atoms, preferably 2 to 6 carbon atoms ("lower alkenyl"), and sometimes more preferably 2 to 4 carbon atoms ("$C_2$-$C_4$ alkenyl"), which is connected with the rest of the molecular moiety through a single bond. Representative examples of alkenyl include, but are not limited to, vinyl, propenyl, allyl, butenyl, etc.

The term "nitroalkane", as used herein, means a compound of Formula R—$NO_2$, where R stands for alkyl as defined above. Representative examples of nitroalkane include, but are not limited to, nitromethane, nitroethane, nitropropane, nitrobutane, etc.

The singular forms "a", "an", and "the" include plural reference, and vice versa, unless the context clearly dictates otherwise.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, in the case of $(CR_5R_6)_n$ where n is an integer from 0 to 20, a numerical value range of "0 to 20" should be interpreted to include not only the explicitly recited numerical value of 0 to 20, but also the individual numerical values (e.g., 1, 2, 3, 5, 10, and 15) and the sub-ranges (e.g., 0-3, 1-3, 1-5, 5-10, 10-15) within the indicated range.

Herein, this application discloses an improved method of preparing a cyclic allylic nitro compound of Formula (I):

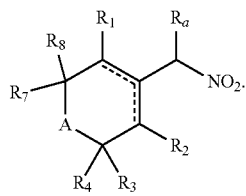

In Formula (I), one of the two ═══ is a double bond, and the other is a single bond, and in the case of an asymmetric ring, the two different double bond positions are referred to as α-isoform and β-isoform respectively; $R_a$ is H or methyl; at least one of $R_1$ and $R_2$ is hydrogen, the other one is hydrogen or methyl; A is $(CR_5R_6)_n$, where n is an integer from 0 to 20 (for example, 0-3, 0-5, 0, 1, 2, and 3), each of $R_3$, $R_4$, $R_5$, $R_6$, $R_7$, and $R_8$, independently, is hydrogen, $C_1$-$C_4$ alkyl (for example, methyl), or $C_2$-$C_4$ alkenyl (for example, 1-methyl-vinyl).

The preparation method of the cyclic allylic nitro compound comprises a nitro-aldol reaction between a cyclic ketone and nitroalkane, wherein the nitroalkane is defined as above, and the cyclic ketone is a compound of Formula (II):

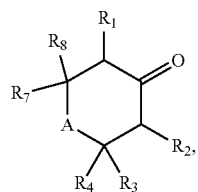

where $R_1$, $R_2$, A, $R_3$, $R_4$, $R_7$, and $R_8$ have the same meanings as those in Formula (I).

The nitro-aldol reaction is conducted in the presence of a nitro-aldol catalyst in a solvent to obtain a nitro-aldol reaction mixture containing the product cyclic allylic nitro compound. The process of this invention unexpectedly gives a high selectivity and high yield towards the desired α-isomer product of a cyclic allylic nitro compound.

Not to be bound by any theory, the desirable regioselectivity can be explained by considering the steric effects involved in the deprotonation of the diamine adduct 17 (Scheme 4). The presence of a gem-dimethyl group on the ring and the N-dimethyl functionality gives rise to a preference towards deprotonation at the α-carbon due to less steric interactions, giving the α-product 16a preferentially.

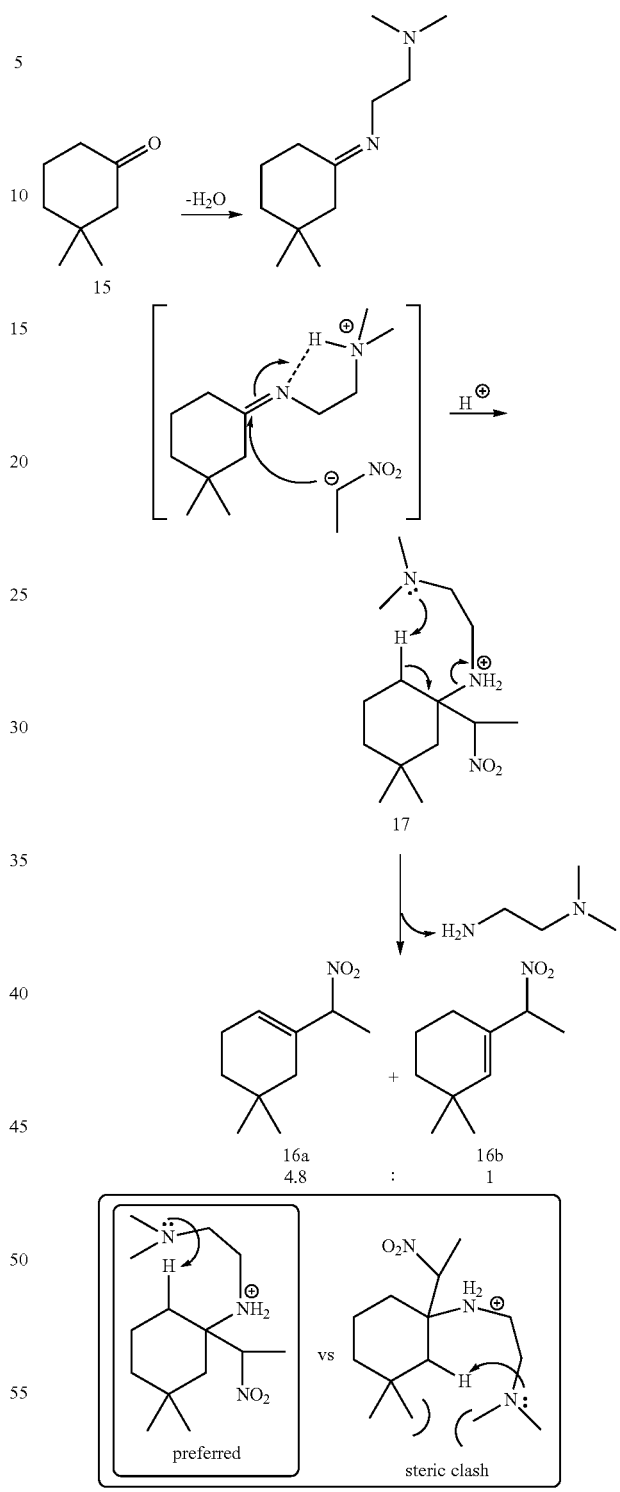

Concentration of the cyclic ketone relates to the reaction rate and thus reaction time. Upon increasing the concentration, the internal reactor temperature also increased due to the increased ratio of the high boiling-point solvent nitroethane (b.p., 114° C.) to the low boiling-point solvent ethyl acetate ("EtOAc", b.p. 77° C.). Preferably, the reaction temperature is kept below a temperature (e.g., 100° C. or below, 90° C. or below, and 80° C. or below) to avoid significant evaporation of the amine catalyst, which would become trapped in the aqueous layer of the Dean-Stark trap. Carrying out the reaction neat (namely, free of a solvent) is optional and possible provided that water is removed from the reaction mixture successfully. Exemplary amine catalysts include those shown in the table below.

| Amine catalyst | b.p./°C. |
| --- | --- |
| 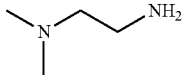 12 | 105 |
| 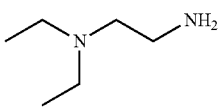 18 | 146 |
| 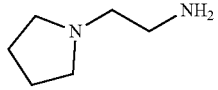 19 | 160 |
| 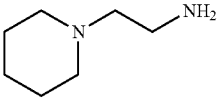 20 | 186 |
| 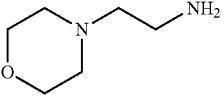 21 | 224 |
| 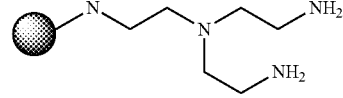 22 | — |
| 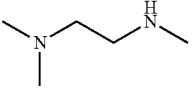 23 | 117 |
| 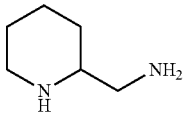 24 | 190 |
| 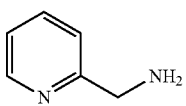 25 | 200 |
| 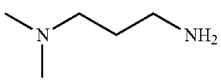 26 | 133 |

-continued

| Amine catalyst | b.p./°C. |
| --- | --- |
| 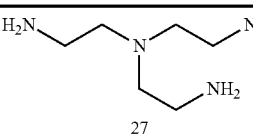 27 | 240 |
| 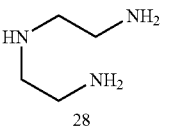 28 | 200 |

Typical amounts of the nitro-aldol catalyst (e.g., the amine catalyst) vary from 5 to 100% by mole of the cyclic ketone (hereinafter mol %), with a lower limit of 5 mol %, 7 mol %, 10 mol %, or 15 mol % and an upper limit of 100 mol %, 90 mol %, 80 mol %, 70 mol %, or 60 mol %. Preferably, the amount of the nitro-aldol catalyst is 15-60 mol %. The amount of nitroalkane, preferably, is 2 equivalents or more relative to the cyclic ketone, e.g., 2 to 100 equivalents with a lower limit of 2, 2.5, or 5 equivalents, and an upper limit of 100, 80, 50, 20, or 10 equivalents.

In some embodiments, the nitro-aldol reaction time is kept at 1 to 48 hours with a lower limit of 1, 2, 4, 7, 10, or 16 hours and an upper limit of 48, 36, 30, or 24 hours (e.g., 2 to 36 hours, 10 to 30 hours, and 16 to 24 hours).

The cyclic allylic nitro compound, i.e., the nitro-aldol reaction product, can be purified or isolated from the nitro-aldol reaction mixture by conventional separation methods such as extraction, distillation, and chromatography. In some embodiments, the cyclic allylic nitro compound is isolated by distillation. Preferably, the nitro-aldol reaction mixture is washed with an acid aqueous solution before the distillation to remove side products and/or the amine catalyst. An exemplary acid aqueous solution is a 1 mol/L HCl aqueous solution. In some embodiments, the nitroalkane or amine catalyst is removed by distillation from the nitro-aldol reaction mixture before the acid wash step. The nitroalkane is typically more dense than water and its presence leads to poor phase separation during the acid wash step. In some embodiments, the nitroalkane and/or amine catalyst are recovered and reused.

It is possible to add the amine catalyst in portions. In some embodiments, a first portion of the amine catalyst (e.g., 1 to 15 mol % relative to the cyclic ketone) is added to a first reaction mixture containing the cyclic ketone, nitroalkane, and solvent before the nitro-aldol reaction; a second portion of the amine catalyst (e.g., 1 to 15% mol % relative to the cyclic ketone) is added to the first reaction mixture 1 to 5 hours after the first reaction mixture reaches a predetermined reaction temperature (e.g., 50 to 110° C.) to obtain a second reaction mixture; and, optionally, a third portion of the amine catalyst (e.g., 1 to 15 mol % relative to the cyclic ketone) is added to the second reaction mixture 1 to 5 hours after the addition of the second portion of the amine catalyst obtain a third reaction mixture.

Another aspect of this invention relates to a method of preparing α-dehydroherbac. The method includes the step of (a) obtaining 5,5-dimethyl-1-(1-nitroethyl)cyclohex-1-ene according to the method described above, and (b) a Nef reaction of 5,5-dimethyl-1-(1-nitroethyl)cyclohex-1-ene to obtain α-dehydroherbac.

Since the discovery of the Nef reaction in 1894 (Nef, *Liebigs Ann. Chem.* 1894, 280, 263-291), a variety of alternative conditions to the classical base-acid treatment have been reported (Ballini et al., *Adv. Synth. Catal.* 2015, 357, 2371-2402). Interesting examples include the use of oxone (Ceccherelli et al., *Synth. Commun.* 1998, 28, 3057-3064), organic bases such as DABCO (Umemiya et al., *Chem. Eur. J.* 2014, 20, 15753-15759) and DBU (Ballini et al., M. *Tetrahedron Lett.* 2002, 43, 5233-5235) and biocatalytic methods (Francis et al., *Biol. Chem.* 2005, 280, 5195-5204; Durchschein et al., *Org. Biomol. Chem.* 2011, 9, 3364-3369).

The Nef reaction of 5,5-dimethyl-1-(1-nitroethyl)cyclohex-1-ene preferably includes (b1) nitronate salt formation by contacting 5,5-dimethyl-1-(1-nitroethyl)cyclohex-1-ene with NaOH, (b2) contacting the nitronate salt with an acid such as sulfuric acid ($H_2SO_4$), hydrochloric acid (HCl), or both. In some embodiments, NaOH is used at a level of 0.5 to 5 equivalents (e.g., 0.75 to 2.5 equivalents, 1 to 1.5 equivalents, and 1.1 to 1.4 equivalents) relative to 5,5-dimethyl-1-(1-nitroethyl)cyclohex-1-ene. In other embodiments, the acid is added at −5 to 15° C. at a level of 1 to 10 equivalents (e.g., 1 to 5 equivalents and 1.5 to 4 equivalents).

In conclusion, an improved method of preparing a cyclic allylic nitro compound via nitro-aldol reaction is disclosed, in which conventional solvent benzene is replaced with a greener solvent, and the reaction conditions disclosed herein unexpectedly give desired selectivity and high yield.

In particular, a facile method for the synthesis of α-dehydroherbac has been developed which gives high selectivity towards the desired double bond isomer. The methods of this invention offer an economic effective and green process of preparing α-dehydroherbac. Cyclic allylic nitro compounds prepared by the methods of this invention provides a class of synthetically versatile building blocks, and can be further converted to useful α,β-unsaturated ketones.

The invention is described in greater detail by the following non-limiting examples. Without further elaboration, it is believed that one skilled in the art can, based on the description herein, utilize the present invention to its fullest extent.

EXAMPLES

General Method

Unless otherwise stated, all solvents were purchased from Fisher Scientific and used without further purification. Substrates and their precursors and reagents were purchased from Alfa Aesar or Sigma Aldrich and used as received.

$^1$H-NMR spectra were recorded on either Bruker Avance-400 or Varian VNMRS-700 instruments and are reported relative to residual solvent: $CHCl_3$ (δ 7.26 ppm). $^{13}$C-NMR spectra were recorded on the same instruments and are reported relative to $CHCl_3$ (δ 77.16 ppm). Data for $^1$H-NMR are reported as follows: chemical shift (δ/ppm) (multiplicity, coupling constant (Hz), integration). Multiplicities are reported as follows: s=singlet, d=doublet, t=triplet, q=quartet, p=pentet, m=multiplet, br. s=broad singlet, app.=apparent. Data for $^{13}$C-NMR are reported in terms of chemical shift ($δ_C$/ppm). DEPT-135, COSY, HSQC, HMBC and NOESY experiments were used in structural assignments.

IR spectra were obtained using a Perkin Elmer Spectrum Two UATR Two FT-IR Spectrometer (neat, ATR sampling) with the intensities of the characteristic signals being reported as weak (w, <20% of tallest signal), medium (m, 21-70% of tallest signal) or strong (s, >71% of tallest signal). Low and high resolution mass spectrometry was performed using the indicated techniques. Gas chromatography mass spectrometry (GC-MS) was performed on a Shimadzu QP2010-Ultra equipped with an Rxi-5Sil MS column in EI mode. Atmospheric solids analysis probe mass spectrometry (ASAP-MS) was performed using a Waters LCT Premier XE. For accurate mass measurements the deviation from the calculated formula is reported in ppm.

Starting Material 3,3-Dimethylcyclohexanone 15

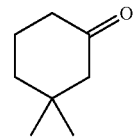

Chemical Formula: $C_8H_{14}O$
Molecular Weight: 126.20

Prepared via selective hydrogenation of dimedone according to the literature (US 20120283476). $^1$H NMR (400 MHz, $CDCl_3$) δ 2.31-2.25 (m, 2H), 2.16 (t, J=0.8 Hz, 2H), 1.94-1.85 (m, 2H), 1.62-1.57 (m, 2H), 0.99 (s, 6H); $^{13}$C NMR (101 MHz, $CDCl_3$) δ 212.3, 55.0, 40.9, 38.0, 36.1, 28.6, 22.5 ppm; FT-IR $v_{max}$ 503 (w), 1076 (w), 1225 (m), 1291 (w), 1368 (w), 1455 (w), 1708 (s), 2954 (m, br); GC-MS $R_t$ 2.60 min, m/z 126 [M]$^+$, 111 [M-Me]$^+$.

Representative Procedure for the Amine-Catalyzed Irregular Nitro-Aldol Reaction

A mixture of 3,3-dimethylcyclohexanone (15, 40 g, 0.305 mol), N,N-diethylethylenediamine (18, 4.3 mL, 10 mol %), EtOAc (30 mL) and nitroethane (214 mL, 10 equiv.) was stirred in a round-bottom flask equipped with Dean-Stark trap (pre-filled with EtOAc) and reflux condenser and heated to 100° C. After a total of 22 hours the reaction was cooled to room temperature (i.e., 25° C.) and the nitroethane and EtOAc were removed under reduced pressure. EtOAc (100 mL) was added and amine residues were removed by washing with 1M HCl (2×100 mL). The remaining solution was distilled in vacuo to give the product cyclic allylic nitro compounds 16a and 16b at a yield of 78% with the ratio between 16a (the α product) and 16b (the β product) of 5.4:1.

Examples 1-13

The representative procedure described above was followed except for the reagents, their amounts, reaction time, yields, and work-up steps (removal of solvent and nitroethane, washing with HCl, which are shown below in Tables 1 and 2.

5, 5-Dimethyl-1-(1-nitroethyl)cyclohex-1-ene 16a

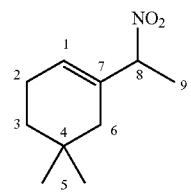

Chemical Formula: $C_{10}H_{17}NO_2$
Molecular Weight: 183.25

Obtained by reaction of nitroethane with 3,3-dimethyl cyclohexanone as a pale yellow liquid, isolated by vacuum distillation (b.p. 105-110° C./10 mbar). $^1$H NMR (400 MHz, CDCl$_3$) δ 5.90 (m, 1H, 1), 5.00 (q, J=7.6 Hz, 1H, 8), 2.14 (m, 2H, 6), 1.88-1.71 (qq, J=18.9, 2.0 Hz, 2H, 2), 1.62 (d, J=6.8 Hz, 3H, 9), 1.39-1.33 (m, 2H, 3), 0.93 (s, 3H, 5), 0.91 (s, 3H, 5) ppm; $^{13}$C NMR (101 MHz, CDCl$_3$) δ 132.0 (7), 128.4 (1), 88.3 (8), 37.8 (2), 34.4 (3), 28.8 (4), 28.3 (5), 27.4 (5), 23.2 (6), 16.9 (9) ppm; FT-IR $v_{max}$ 663 (w), 860 (w), 1364 (w), 1384 (m), 1449 (w), 1545 (s), 2918 (w); GC-MS R$_t$ 3.71 min, m/z 137 [M-NO$_2$]$^+$; HRMS m/z found [M+H]$^+$ 184.1344, $C_{10}H_{18}NO_2$ requires 184.1338 (Δ=3.3 ppm).

3,3-Dimethyl-1-(1-nitroethyl)cyclohex-1-ene 16b

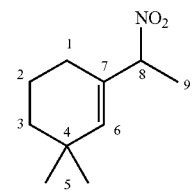

Chemical Formula: $C_{10}H_{17}NO_2$
Molecular Weight: 183.25

Obtained by reaction of nitroethane with 3,3-dimethyl cyclohexanone as a pale yellow liquid, isolated by vacuum distillation (b.p. 105-110° C./10 mbar). $^1$H NMR (600 MHz, CDCl$_3$) δ 5.59 (s, 1H, 6), 4.92 (q, J=7.0 Hz, 1H, 8), 2.02-1.87 (m, 2H, 1), 1.67-1.62 (m, 2H, 2), 1.62 (d, J=6.8 Hz, 3H, 9), 1.45-1.35 (m, 2H, 3), 0.98 (s, 3H, 5), 0.97 (s, 3H, 5) ppm; $^{13}$C NMR (151 MHz, CDCl$_3$) δ 139.5 (6), 130.8 (7), 88.3 (8), 36.5 (3), 32.0 (4), 29.6 (5), 29.2 (5), 24.3 (1), 19.4 (2), 17.0 (9) ppm; FT-IR $v_{max}$ 663 (w), 860 (w), 1364 (w), 1384 (m), 1449 (w), 1545 (s), 2918 (w); GC-MS R$_t$ 3.61 min, m/z 137 [M-NO$_2$]$^+$; HRMS m/z found [M+H]$^+$ 184.1344, $C_{10}H_{18}NO_2$ requires 184.1338 (Δ=3.3 ppm).

In Example 1, the representative procedure was followed using 3,3-dimethylcyclohexanone (15), N,N-dimethylethylenediamine (12), isopropyl acetate ($^i$PrOAc) and nitroethane (EtNO$_2$). The reaction mixture was refluxed for 18 hours.

In Example 2, the same procedure as Example 1 was followed except that ethyl acetate (EtOAc) was used instead of PrOAc and the reaction was run for 22 hours instead of 18 hours.

A comparative reaction, i.e., Comparative 1, was performed following the same procedure as Example 1, except that benzene was used instead of PrOAc and the reaction was run for 24 hours.

The yields of compounds 16a (α-product) and 16b (β-product) for were shown in Table 1 below. Isopropyl acetate worked well as a solvent giving 64% conversion with a 4.8:1 α-selectivity. This result was reproduced with ethyl acetate at a concentration of 1 M.

Each of Examples 3-5 was performed following the same procedure as Example 2 except that a different nitro-aldol catalyst (an amine base) was used. See Table 2 below.

TABLE 1

Nitro-aldol reaction in isopropyl acetate and ethyl acetate

| Examples | Solvent | Time | EtNO$_2$ | 16a Yield$^a$ | 16b-Yield$^a$ |
|---|---|---|---|---|---|
| Comparative 1 | Benzene | 24 h | 10 equiv. | 28% | 6% |
| 1 | $^i$PrOAc$^b$ | 18 h | 10 equiv. | 53% | 11% |
| 2 | EtOAc$^c$ | 22 h | 10 equiv. | 53% | 11% |

Reactions conducted on 5 mmol scale at 0.2M unless stated otherwise.
$^a$Yield estimated by GC-MS using n-pentadecane as an internal standard.
$^b$Loss of solvent through evaporation observed.
$^c$Reaction carried out at 1M.

TABLE 2

Nitro-aldol reaction using different catalysts

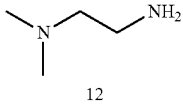

| Examples | Base | b.p./°C. | Yield[a] (16a:16b) |
|---|---|---|---|
| 2 | 12 | 105 | 64% (4.9) |
| 3 | 18 | 146 | 80% (5.3) |
| 4 | 19 | 160 | 81% (8.2) |
| 5 | 20 | 186 | 70% (4.8) |

Reactions carried out on 50 mmol scale at 1M.
[a]Yield estimated by GC-MS using n-pentadecane as an internal standard.

As shown in Table 2 above, diethylethylene diamine (18), 1-(2-aminoethyl)pyrrolidine (19), and 1-(2-aminoethyl)piperidine (20) each effectively catalyzed the nitro-aldol reaction, giving a yield of 80%, 81%, and 70%, respectively, and a selectivity (i.e., the ratio of 16a:16b) of 5.3, 8.2, and 4.8, respectively.

In Examples 6-10, the nitro-aldol catalyst diethylethylene diamine 18 was used at from 5 mol % to 100 mol % relative to the cyclic ketone 15. See Table 3 below. In Examples 11-13, nitroethane was used at a level of 2.5, 5, and 10 equivalents, respectively, relative to the cyclic ketone 15. See Table 4 below. Acceptable yields and selectivity were obtained for both nitro-aldol catalyst and nitroethane at the levels used in Examples 6-13.

TABLE 3

Variation of base stoichiometry

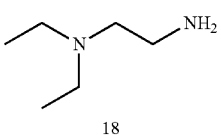

| Entry | base equiv. | Yield[a] | α:β ratio |
|---|---|---|---|
| 6 | 5 mol % | 37% | 2.0 |
| 7 | 15 mol % | 67% | 4.4 |
| 8 | 30 mol % | 80% | 5.3 |

TABLE 3-continued

Variation of base stoichiometry

| Entry | base equiv. | Yield[a] | α:β ratio |
| --- | --- | --- | --- |
| 9 | 60 mol % | 66% | 4.9 |
| 10 | 100 mol % | 41% | 3.0 |

Reactions carried out on 50 mmol scale at 1M.
[a]Yield estimated by GC-MS using n-pentadecane as an internal standard.

TABLE 4

Variation of nitroethane stoichiometry

| Entry | EtNO$_2$ equiv. | Yield[a] | a: ratio |
| --- | --- | --- | --- |
| 11 | 2.5 | 33% | 5.6 |
| 12 | 5 | 62% | 5.7 |
| 13 | 10 | 80% | 5.3 |

Reactions carried out on 50 mmol scale at 1.0M.
[a]Yield estimated by GC-MS using n-pentadecane as an internal standard.

Examples 14-16

Products 16a and 16b were purified using various work-up conditions in Examples 14-16. In Example 14, the reaction was performed at 0.5-mole scale following the representative procedure above. The resultant reaction mixture was washed with 1 M aqueous solution and extracted with EtOAc into an oil phase, which was then distilled to give the products with a yield of 73% and the ratio between 16a and 16b of 5.7:1.

In Example 15, the same reaction described in Example 14 was performed. The resultant reaction mixture was distilled under vacuum to give the products with a yield of 76% and the ratio between 16a and 16b of 5.2:1. However, the purified products were not as pure as the products in Example 14. Impurities and side products were found in the final purified products.

In Example 16, nitroethane was added in three portions. More specifically, a mixture of 3,3-dimethylcyclohexanone (15, 40 g, 0.305 mol), N,N-diethylethylenediamine (18, 4.3 mL, 10 mol %), EtOAc (30 mL) and nitroethane (214 mL, 10 equiv.) was stirred in a round-bottom flask equipped with Dean-Stark trap (pre-filled with EtOAc) and reflux condenser and heated to 100° C. After 3 hours, a second portion of N,N-diethylethylenediamine (4.3 mL, 10 mol %) was added and a third portion (4.3 mL, 10 mol %) was added after a further 3 hours. After a total of 22 hours the reaction was cooled to room temperature (i.e., 25° C.) and the nitroethane and EtOAc were removed under reduced pressure. EtOAc (100 mL) was added and N,N-diethylethylenediamine residues were removed by washing with 1M HCl (2×100 mL). The remaining solution was concentrated in vacuo to give the products with a yield of 78% and the ratio between 16a and 16b of 5.4:1.

Example 17. 1-(1-Nitroethyl)cyclohept-1-ene 34

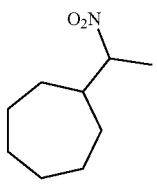

Chemical Formula: $C_9H_{15}NO_2$
Molecular Weight: 169.22

Obtained by reaction of nitroethane with cycloheptanone as a yellow liquid (50.0 mmol scale, 5.17 g, 61%), isolated by $SiO_2$ column chromatography (hexane:EtOAc, 95:5), $R_f$ (8:2, hexane:EtOAc) 0.7. $^1$H NMR (400 MHz, CDCl$_3$) δ 6.05 (t, J=6.5 Hz, 1H), 4.99 (q, J=6.9 Hz, 1H), 2.25-2.18 (m, 4H), 1.81-1.74 (m, 2H), 1.62 (d, J=6.8 Hz, 3H), 1.59-1.44 (m, 4H) ppm; $^{13}$C NMR (101 MHz, CDCl$_3$) δ 139.4, 134.8, 89.5, 32.3, 28.4, 28.3, 26.6, 26.2, 17.3 ppm; FT-IR $v_{max}$ 861 (m), 1354 (m), 1384 (m), 1447 (m), 1544 (s), 2850 (w), 2921 (m); GC-MS $R_t$, 3.63 min, m/z 123 [M-NO$_2$]$^+$.

Example 18. 1-(1-Nitroethyl)cyclooct-1-ene 35

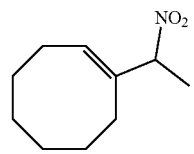

Chemical Formula: $C_{10}H_{17}NO_2$
Molecular Weight: 183.25

Obtained by reaction of nitroethane with cyclooctanone as a pale yellow liquid (50.0 mmol scale, 3.60 g, 39%), isolated by $SiO_2$ column chromatography (hexane:EtOAc, 95:5), $R_f$ (9:1, hexane:EtOAc) 0.5. $^1$H NMR (400 MHz, CDCl$_3$) δ 5.90 (t, J=8.2 Hz, 1H), 5.05 (q, J=6.8 Hz, 1H), 2.33-2.26 (m, 2H), 2.24-2.16 (m, 2H), 1.65 (d, J=6.8 Hz, 3H), 1.60-1.42 (m, 8H) ppm; $^{13}$C NMR (101 MHz, CDCl$_3$) δ 135.6, 132.7, 88.5, 29.4, 29.0, 26.3, 26.3, 26.2, 26.1, 17.6 ppm; FT-IR $v_{max}$, 758 (w), 860 (w), 1359 (w), 1383 (w), 1449 (w), 1469 (w), 1545 (s), 2852 (w), 2926 (m); GC-MS $R_t$ 4.05 min, m/z 137 [M-NO$_2$]$^+$.

Example 19. 3, 5, 5-Trimethyl-1-(1-nitroethyl)cyclohex-1-ene/3, 3, 5-trimethyl-1-(1-nitroethyl)cyclohex-1-ene 36a+36b

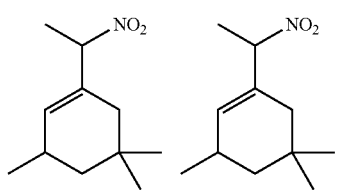

Chemical Formula: $C_{11}H_{19}NO_2$
Molecular Weight: 197.28

Obtained by reaction of nitroethane with cyclooctanone as a pale yellow liquid (50 mmol scale, 2.51 g, 25%), isolated by $SiO_2$ column chromatography (hexane:EtOAc, 95:5), $R_f$ (9:1, hexane:EtOAc) 0.4. Obtained as a mixture of endo double bond isomers along with the two corresponding exo isomers. NMR spectra of mixture not resolved; FT-IR $v_{max}$, 1362 (m), 1384 (m), 1456 (m), 1520 (s), 1548 (s), 2907 (m), 2952 (m); GC-MS $R_t$ 3.74+3.69 min, m/z 151 [M-NO$_2$]$^+$; HRMS m/z found [M+H]$^+$ 198.1483, $C_{11}H_{20}NO_2$ requires 198.1494 (Δ=5.6 ppm).

Example 20. 5,5-Dimethyl-1-(nitromethyl)cyclohex-1-ene 37a

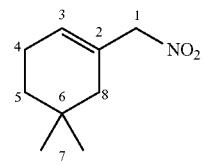

Chemical Formula: $C_9H_{15}NO_2$
Molecular Weight: 169.22
Numbers used for assigning NMR peaks Obtained by reaction of nitromethane with 3,3-dimethylcyclohexanone as a pale yellow liquid (55 mmol scale, 8.8 g, 94%), isolated by $SiO_2$ column chromatography (hexane:EtOAc, 98:2) as a mixture of double bond isomers (3:1, 37a:37b), $R_f$ (9:1, hexane:EtOAc) 0.7. $^1$H NMR (700 MHz, CDCl$_3$) δ 5.91-5.88 (m, 1H, 3), 4.79 (s, 2H, 1), 2.16-2.12 (m, 2H, 4), 1.84 (s, 2H, 8), 1.34 (t, J=6.4 Hz, 2H, 5), 0.92 (s, 6H, 7) ppm; $^{13}$C NMR (176 MHz, CDCl$_3$) δ 132.0 (3), 127.4 (2), 82.7 (1), 40.3 (8), 34.2 (5), 29.0 (6), 27.9 (7), 23.3 (4) ppm; FT-IR $v_{max}$ 665 (w), 1367 (m), 1428 (w), 1550 (s), 2920 (w, br); GC-MS $R_t$ 3.42 min, m/z 123 [M-NO$_2$]$^+$; HRMS m/z found [M+H]$^+$ 170.1186, $C_9H_{16}NO_2$ requires 170.1181 (Δ=2.9 ppm).

3,3-Dimethyl-1-(nitromethyl)cyclohex-1-ene 37b

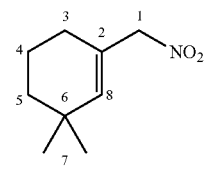

Chemical Formula: $C_9H_{15}NO_2$
Molecular Weight: 169.22
Numbers used for assigning NMR peaks Obtained by reaction of nitromethane with 3,3-dimethylcyclohexanone as a pale yellow liquid (55.0 mmol scale, 8.80 g, 94%), isolated by $SiO_2$ column chromatography (hexane:EtOAc, 98:2) as a mixture of double bond isomers (3:1, 37a:37b), $R_f$ (9:1, hexane:EtOAc) 0.7. $^1$H NMR (700 MHz, CDCl$_3$) δ 5.64-5.61 (m, 1H, 8), 4.77 (s, 2H, 1), 2.01 (t, J=6.3 Hz, 2H, 3), 1.70-1.65 (m, 2H, 4), 1.43-1.40 (m, 2H, 5), 1.00 (s, 6H, 7) ppm; $^{13}$C NMR (176 MHz, CDCl$_3$) δ 143.0 (8), 126.2 (2), 82.8 (1), 36.2 (5), 32.3 (6), 29.3 (7), 26.6 (3), 19.3 (4) ppm; FT-IR $v_{max}$ 665 (w), 1367 (m), 1428 (w), 1550 (s), 2920 (w, br); GC-MS $R_t$ 3.37 min, m/z 123 [M-NO$_2$]$^+$; HRMS m/z found [M+H]$^+$ 170.1186, $C_9H_{16}NO_2$ requires 170.1181 (Δ=2.9 ppm).

Example 21. 1-(Nitromethyl)cyclohept-1-ene 38

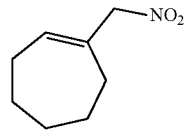

Chemical Formula: $C_8H_{13}NO_2$
Molecular Weight: 155.20

Obtained by reaction of nitromethane with cycloheptanone as a yellow liquid (50 mmol scale, 5.83 g, 75%), isolated by SiO$_2$ column chromatography (hexane:EtOAc, 95:5), $R_f$ (8:2, hexane:EtOAc) 0.6. $^1$H NMR (400 MHz, CDCl$_3$) δ 6.07 (t, J=6.4 Hz, 1H), 4.84 (d, J=0.8 Hz, 2H), 2.34-2.16 (m, 4H), 1.84-1.73 (m, 2H), 1.65-1.50 (m, 4H) ppm; $^{13}$C NMR (101 MHz, CDCl$_3$) δ 138.4, 134.4, 84.4, 31.9, 31.3, 28.6, 26.3, 26.2 ppm; FT-IR $v_{max}$ 643 (m), 848 (w), 1306 (w), 1370 (m), 1447 (w), 1547 (s), 2851 (w), 2923 (m); GC-MS $R_t$ 3.50 min, m/z 109 [M-NO$_2$]$^+$.

Example 22. 6-Methyl-1-(nitromethyl)-3-(prop-1-en-2-yl)cyclohex-1-ene 39a

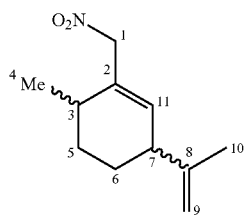

Chemical Formula: $C_{11}H_{17}NO_2$
Molecular Weight: 195.26
Numbers used for assigning NMR peaks Obtained by reaction of nitromethane with dihydrocarvone as a pale yellow liquid (50 mmol scale, 8.65 g, 89%), purified by SiO$_2$ column chromatography (hexane:EtOAc, 95:5) as a mixture of diastereoisomers 39a along with the double bond isomer, 39b (39a:39b=3.3:1), $R_f$ (8:2, hexane:EtOAc) 0.6. $^1$H NMR (700 MHz, CDCl$_3$) δ 5.80 (s, 1H, 11), 5.04-4.98 (m, 1H, 1), 4.80 (m, 1H, 9), 4.79-4.74 (m, 1H, 1), 4.69 (m, 1H, 9), 2.85-2.77 (m, 1H, 7), 2.33-2.27 (m, 1H, 3), 1.89-1.67 (m, 2×1H, 5+6), 1.74-1.71 (m, 3H, 10), 1.59-1.42 (m, 1+0.5H, 6+0.5(5)), 1.32 (m, 0.5H, 5), 1.06 (dd, J=7.1, 3.7 Hz, 3H, 4) ppm; $^{13}$C NMR (176 MHz, CDCl$_3$) δ (147.6+147.5, 8), (136.8+136.3, 11), (133.6+133.4, 2), (111.5+111.2, 9), (80.6+80.4, 1), (43.7+43.3, 7), (30.5+30.0, 3), (29.5+28.8, 5), (25.0+23.5, 6), (21.1+21.0, 10), (19.0+18.9, 4) ppm. FT-IR $v_{max}$ 892 (m), 1372 (m), 1428 (w), 1549 (s), 1644 (w), 2936 (w); GC-MS $R_t$ 3.94+3.96 min, m/z 149 [M-NO$_2$]$^+$; HRMS m/z found [M+H]$^+$ 196.1326, $C_{11}H_{18}NO_2$ requires 196.1338 (Δ=6.1 ppm).

1-Methyl-2-(nitromethyl)-4-(prop-1-en-2-yl)cyclohex-1-ene 39b

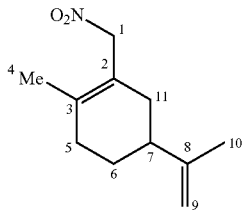

Chemical Formula: $C_{11}H_{17}NO_2$
Molecular Weight: 195.26
Numbers used for assigning NMR peaks Obtained by reaction of nitromethane with dihydrocarvone as a pale yellow liquid (50 mmol scale, 8.65 g, 89%), purified by SiO$_2$ column chromatography (hexane:EtOAc, 95:5) as a mixture of diastereoisomers 39a along with the double bond isomer, 39b (39a:39b=3.3:1), $R_f$ (8:2, hexane:EtOAc) 0.6. $^1$H NMR (700 MHz, CDCl$_3$) δ 4.98-4.89 (dd, J=41.8, 6.0 Hz, 2H, 1), 4.73 (m, 1H, 9), 4.70-4.69 (m, 1H, 9), 2.22-2.02 (m, 5H, 5, 7, 11), 1.81 (m, 1H, 6), 1.78 (s, 3H, 4), 1.73 (s, 3H, 10), 1.46-1.42 (m, 1H, 6) ppm; $^{13}$C NMR (176 MHz, CDCl$_3$) δ 148.8, 138.5, 120.4, 109.1, 78.0, 41.1, 34.0, 32.5, 27.3, 20.7, 19.2 ppm; FT-IR $v_{max}$ 892 (m), 1372 (m), 1428 (w), 1549 (s), 1644 (w), 2936 (w); GC-MS $R_t$ 4.09 min, m/z 149 [M-NO$_2$]$^+$; HRMS m/z found [M+H]+ 196.1326, $C_{11}H_{18}NO_2$ requires 196.1338 (Δ=6.1 ppm).

General Procedure for the Nef Reaction of Nitro Olefins

The cyclic allylic nitro compound 16 (15 g, 82 mmol) was dissolved in ethanol (140 mL) and NaOH (4.1 g, 1.25 equiv.) was added. The resultant mixture was stirred at 25° C. for 30 minutes after which time a nitronate salt had precipitated. The suspension was cooled to 0° C. and a solution of H$_2$SO$_4$ (8.75 mL, 2 equiv.) in H$_2$O (41 mL) was added. After 1 hour of stirring at 0° C. the reaction was allowed to warm to 25° C. and stirred for 2 hours. Ethanol was then removed under reduced pressure and the residue was neutralized with aqueous NaOH solution. The ketone product was extracted with dichloromethane (3×60 mL) and the combined organic layers were concentrated under reduced pressure. Pure product was obtained according to the indicated method in Examples 23-26.

Example 23. 1-(5,5-Dimethylcyclohex-1-en-1-yl)ethanone 13a

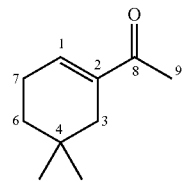

Chemical Formula: $C_{10}H_{16}O$
Molecular Weight: 152.24
Numbers used for assigning NMR peaks Obtained from 16 (82 mmol scale, 8.11 g, 65%, 13a: 13b=5.4:1), isolated by vacuum distillation (b.p. 85-95° C./9 mbar). $^1$H NMR (700 MHz, CDCl$_3$) δ 6.87 (m, 1H, 1), 2.28 (m(obscured), 2H, 7), 2.28 (s, 3H, 9), 2.01 (q, J=2.2 Hz, 2H, 3), 1.34 (t, J=6.4 Hz, 2H, 6), 0.90 (s, 6H, 5) ppm; $^{13}$C NMR (176 MHz, CDCl$_3$) δ 199.5 (8), 139.7 (1), 138.7 (2), 36.4 (3), 34.2 (6), 28.5 (4), 28.0 (5), 25.3 (9), 24.1 (7) ppm; GC-MS R$_t$ 3.32 min, m/z 152 [N]$^+$, 109 [M-Ac]$^+$; HRMS m/z found [M+H]$^+$ 153.1281, C$_{10}$H$_{17}$O requires 153.1279 (Δ=1.3 ppm).

1-(3,3-Dimethylcyclohex-1-en-1-yl)ethanone 13b

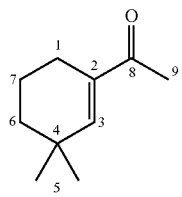

Chemical Formula: C$_{10}$H$_{16}$O
Molecular Weight: 152.24
Numbers used for assigning NMR peaks Obtained from 16 (82.0 mmol scale, 8.11 g, 65%, 13a:13b=5.4:1), isolated by vacuum distillation (b.p. 85-95° C./9 mbar). $^1$H NMR (700 MHz, CDCl$_3$) δ 6.53 (t, J=1.7 Hz, 1H, 3), 2.27 (s, 3H, 9), 2.15 (td, J=6.3, 1.7 Hz, 2H, 1), 1.61 (m, 2H, 7), 1.43 (m, 2H, 6), 1.06 (s, 6H, 5) ppm; $^{13}$C NMR (176 MHz, CDCl$_3$) δ 199.9 (8), 149.7 (3), 137.3 (2), 36.3 (6), 32.7 (4), 29.1 (5), 25.2 (9), 23.1 (1), 19.1 (7) ppm; GC-MS R$_t$ 3.24 min, m/z 152 [M]$^+$, 109 [M-Ac]$^+$; HRMS m/z found [M+H]$^+$ 153.1281, C$_{10}$H$_{17}$O requires 153.1279 (Δ=1.3 ppm).

Example 24. 1-(Cyclohept-1-en-1-yl)ethanone 40

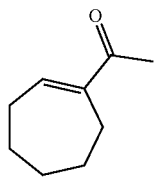

Chemical Formula: C$_9$H$_{14}$O
Molecular Weight: 138.21

Obtained from 34 as a colourless liquid (10.0 mmol scale, 584 mg, 42%), isolated by SiO$_2$ column chromatography (hexane:EtOAc, 95:5), R$_f$ (8:2, hexane:EtOAc) 0.4. $^1$H NMR (400 MHz, CDCl$_3$) δ 7.07 (t, J=6.7 Hz, 1H), 2.50-2.45 (m, 2H), 2.37-2.30 (m, 2H), 2.28 (s, 3H), 1.80-1.73 (m, 2H), 1.58-1.51 (m, 2H), 1.47-1.40 (m, 2H) ppm; $^{13}$C NMR (101 MHz, CDCl$_3$) δ 199.1, 146.5, 145.5, 32.2, 29.1, 26.1, 25.8, 25.3, 25.2 ppm; FT-IR ν$_{max}$ 857 (m), 985 (m), 1198 (m), 1252 (m), 1280 (m), 1350 (m), 1449 (m), 1662 (s), 2850 (m), 2919 (m); GC-MS R$_t$ 3.18 min, m/z 138 [M]$^+$, 95 [M-Ac]$^+$.

Example 25. 1-(Cyclooct-1-en-1-yl)ethanone 41

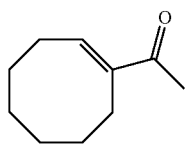

Chemical Formula: C$_{10}$H$_{16}$O
Molecular Weight: 152.24

Obtained from 35 as a colourless liquid (5.8 mmol scale, 417 mg, 47%), isolated by SiO$_2$ column chromatography (hexane:EtOAc, 95:5), R$_f$ (8:2, hexane:EtOAc) 0.4. $^1$H NMR (400 MHz, CDCl$_3$) δ 6.89 (t, J=8.3 Hz, 1H), 2.49-2.44 (m, 2H), 2.39-2.33 (m, 2H), 2.33 (s, 3H), 1.69-1.62 (m, 2H), 1.59-1.41 (m, 6H) ppm; $^{13}$C NMR (101 MHz, CDCl$_3$) δ 199.1, 143.5, 143.1, 29.2, 29.1, 27.5, 26.5, 26.1, 25.4, 23.4 ppm; FT-IR ν$_{max}$ 755 (m), 1199 (m), 1284 (m), 1350 (w), 1383 (w), 1653 (m), 1662 (s), 2852 (m), 2922 (m); GC-MS R$_t$ 3.58 min, m/z 152 [A]$^+$.

Example 25. 1-(3,5,5-Trimethylcyclohex-1-en-1-yl)ethanone 42a

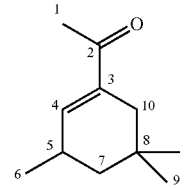

Chemical Formula: C$_{11}$H$_{18}$O
Molecular Weight: 166.26
Numbers used for assigning NMR peaks Obtained from 36 as a colourless liquid (9.29 mmol scale, 695 mg, 54%, 42a:42b=1.9:1), isolated by SiO$_2$ column chromatography (hexane:EtOAc, 95:5), R$_f$ (8:2, hexane:EtOAc) 0.6. $^1$H NMR (600 MHz, CDCl$_3$) δ 6.66 (m, 1H, 4), 2.44-2.38 (m, 1H, 5), 2.29 (s, 3H, 1), 2.19-2.13 (m, 1H, 10), 1.84-1.78 (m, 1H, 10), 1.50-1.45 (m, 1H, 7), 1.09 (d, J=7.2 Hz, 3H, 6), 1.00 (s, 3H, 9), 0.97-0.92 (m, 1H, 7), 0.80 (s, 3H, 9) ppm; $^{13}$C NMR (151 MHz, CDCl$_3$) δ 199.8 (2), 144.9 (4), 137.8 (3), 43.9 (7), 36.5 (10), 31.7 (9), 29.5 (8), 29.5 (5), 25.4 (1), 25.1 (9), 20.7 (6) ppm; FT-IR ν$_{max}$ (mixture) 755 (m), 1248 (m), 1364 (w), 1456 (w), 1635 (m), 1665 (s), 2870 (w), 2954 (m); GC-MS R$_t$ 3.34 min, m/z 166 [1\4]$^+$; HRMS m/z found [M+H]$^+$ 167.1425, C$_{11}$H$_{19}$O requires 167.1436 (Δ=6.6 ppm).

1-(3,3,5-Trimethylcyclohex-1-en-1-yl)ethanone 42b

Step 2: Synthesis of Galbascone from Dimethyl Acetal Intermediate

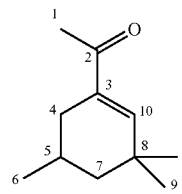

Chemical Formula: $C_{11}H_{18}O$
Molecular Weight: 166.26
Numbers used for assigning NMR peaks

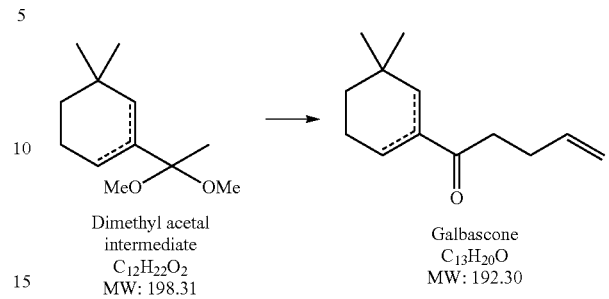

Dimethyl acetal intermediate
$C_{12}H_{22}O_2$
MW: 198.31

Galbascone
$C_{13}H_{20}O$
MW: 192.30

Obtained from 36 as a colourless liquid (9.29 mmol scale, 695 mg, 54%, 42a:42b=1.9:1), isolated by $SiO_2$ column chromatography (hexane:EtOAc, 95:5), $R_f$ (8:2, hexane:EtOAc) 0.6. $^1$H NMR (600 MHz, $CDCl_3$) δ 6.52 (m, 1H, 10), 2.50-2.44 (m, 1H, 4), 2.27 (s, 3H, 1), 1.71-1.63 (m, 1H, 5), 1.56-1.51 (m, 1H, 4), 1.51-1.48 (m, 1H, 7), 1.07 (s, 3H, 9), 1.05 (s, 3H, 9), 1.02 (m, 1H, 7), 0.99 (d, J=6.6 Hz, 3H, 6) ppm; $^{13}$C NMR (151 MHz, $CDCl_3$) δ 199.8 (2), 149.5 (10), 137.0 (3), 45.3 (7), 34.1 (8), 31.8 (4), 30.4 (9), 28.4 (9), 25.6 (5), 25.3 (1), 22.0 (6) ppm; FT-IR $ν_{max}$ (mixture) 755 (m), 1248 (m), 1364 (w), 1456 (w), 1635 (m), 1665 (s), 2870 (w), 2954 (m); GC-MS $R_t$ 3.13 min, m/z 166 [M]$^+$; HRMS m/z found [M+H]$^+$ 167.1425, $C_{11}H_{19}O$ requires 167.1436 (Δ=6.6 ppm).

Example 26

Cyclic allylic ketones 13a and 13b were converted to Galbascone following the procedure below.

Step 1: Synthesis of Dimethyl Acetal Intermediate

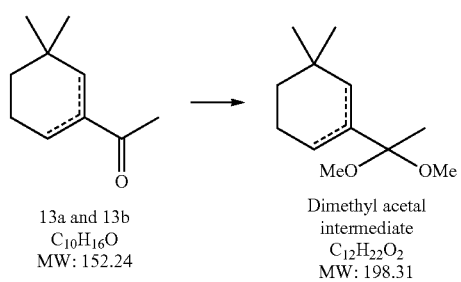

13a and 13b
$C_{10}H_{16}O$
MW: 152.24

Dimethyl acetal intermediate
$C_{12}H_{22}O_2$
MW: 198.31

Into a 5 L reaction vessel equipped with stirrer, thermometer, heater and reflux condenser were added 545 g of methanol, 1,330 g of trimethyl ortho formate and 6 g of a 30% HCl aqueous solution. The resultant reaction mixture was cooled to 0° C. and then 1,900 g of a mixture of α and β-dehydro Herbac (13a and 13b, respectively) were added during a period of 8 hours while maintaining the temperature below 5° C. After the end of the addition, the reaction was stirred for 1 additional hour and quenched with 12 g of sodium methoxide (30% solution in methanol) before heating it up to 80° C., under reduced pressure (100 mmHg), to remove methanol and methyl formate formed by distillation. The resulting concentrated crude (2,435 g) contained the dimethyl acetal intermediates mixture, which was used in the following step without further purification.

Into a 5 L reaction vessel equipped with stirrer, thermometer, heater and reflux condenser were added 2,435 g of dimethyl acetal intermediate from step 1, 30 g of acetic acid glacial, 17 g of sodium acetate and 1.485 g of allyl alcohol. The reaction mixture was slowly heated under stirring to 185° C., while distilling a mixture of methanol and allyl alcohol, and maintained at this temperature for 3 hours until complete conversion of the dimethyl acetal intermediate. Subsequently, the reaction was cooled to room temperature and transferred to a distiller for purification. Fractional distillation of the crude thus obtained afforded 1,710 g (71% overall yield) of α- and β-Galbascone as a mixture.

All references cited herein are incorporated by reference in their entirety. The foregoing examples and description of certain preferred embodiments should be taken as illustrating, rather than as limiting, the present invention. As would be readily appreciated by a person skilled in the art, numerous variations and combinations of the features set forth above can be utilized without departing from the present invention, which are all encompassed by the present invention.

What is claimed is:

1. A method of preparing a cyclic allylic nitro compound, comprising a nitro-aldol reaction between a cyclic ketone and nitroalkane in the presence of an amine catalyst in a solvent, wherein the cyclic allylic nitro compound is a compound of Formula (I),

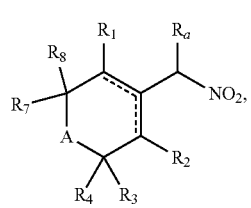

(I)

in which one of the two --- is a double bond, and the other is a single bond, $R_a$ is H or methyl, at least one of $R_1$ and $R_2$ is hydrogen, the other one is hydrogen or methyl, A is $(CR_5R_6)_n$, n is an integer from 0 to 20, each of $R_3$, $R_4$, $R_5$, $R_6$, $R_7$, and $R_8$, independently, is hydrogen, $C_1$-$C_4$ alkyl, or $C_2$-$C_4$ alkenyl;

the cyclic ketone is a compound of Formula (II),

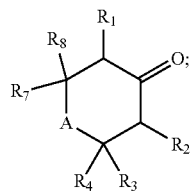

the amine catalyst is a compound of Formula (III):

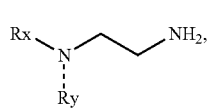

in which each of Rx and Ry, independently, is $C_1$-$C_4$ alkyl, or Rx and Ry, together with nitrogen atom to which they attached, form a pyrrolidine ring or a piperidine ring,
the nitroalkane is nitroethane or nitromethane; and
the solvent is a $C_2$-$C_3$ alkyl acetate.

2. The method of claim 1, wherein the $C_2$-$C_3$ alkyl acetate is ethyl acetate or isopropyl acetate.

3. The method of claim 1, wherein the amine catalyst is selected from the group consisting of:

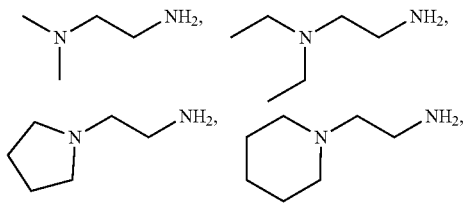

and combinations thereof.

4. The method of claim 1, wherein the amount of the nitroalkane is 1 to 10 equivalents, and the amount of the amine catalyst is 0.1 to 1 equivalents, both relative to the cyclic ketone.

5. The method of claim 1, wherein the nitro-aldol reaction is conducted under reflux and water is removed.

6. The method of claim 5, wherein a Dean-Stark device or a molecular sieve is used to remove water.

7. The method of claim 1, wherein the reaction product is isolated by distillation.

8. The method of claim 7, wherein an acid wash is conducted prior to distillation.

9. The method of claim 1, wherein the amine catalyst is added portion-wise, and the reaction time is 24 hours or less.

10. The method of claim 1, wherein the cyclic ketone is any one selected from the group consisting of:

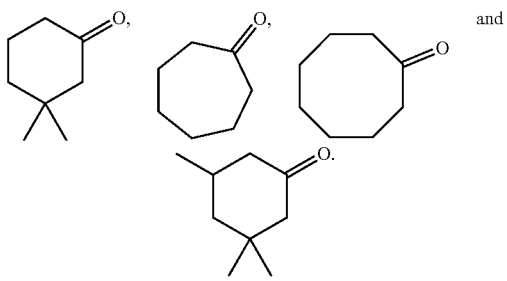

11. The method of claim 10, wherein the cyclic allylic nitro compound is 5,5-dimethyl-1-(1-nitroethyl)cyclohex-1-ene, the cyclic ketone is 3,3-dimethylcyclohexanone, and the nitroalkane is nitroethane.

12. A method of preparing α-dehydroherbac, comprising (a) obtaining 5,5-dimethyl-1-(1-nitroethyl)cyclohex-1-ene according to the method of claim 10, (b) a Nef reaction of 5,5-dimethyl-1-(1-nitroethyl)cyclohex-1-ene to obtain α-dehydroherbac.

13. The method of claim 12, wherein the Nef reaction comprises nitronate salt formation with NaOH, followed by treatment with sulfuric acid, hydrochloric acid, or both.

14. A method of preparing Galbascone, comprising (c) obtaining α-dehydroherbac according to the method of claim 12, and (d) converting α-dehydroherbac to Galbascone.

* * * * *